United States Patent
Toriyabe et al.

(10) Patent No.: US 9,132,068 B2
(45) Date of Patent: Sep. 15, 2015

(54) DENTAL COMPOSITE RESTORATIVE MATERIAL

(75) Inventors: Chika Toriyabe, Tsukuba (JP); Hironobu Akizumi, Tsukuba (JP)

(73) Assignee: TOKUYAMA DENTAL CORPORATION (JP)

(*) Notice: Subject to any disclaimer, the term of this patent is extended or adjusted under 35 U.S.C. 154(b) by 59 days.

(21) Appl. No.: 13/805,302

(22) PCT Filed: Jun. 10, 2011

(86) PCT No.: PCT/JP2011/063337
§ 371 (c)(1),
(2), (4) Date: Dec. 18, 2012

(87) PCT Pub. No.: WO2011/158742
PCT Pub. Date: Dec. 22, 2011

(65) Prior Publication Data
US 2013/0096226 A1 Apr. 18, 2013

(30) Foreign Application Priority Data

Jun. 18, 2010 (JP) ................... 2010-139519
Aug. 26, 2010 (JP) ................... 2010-189440

(51) Int. Cl.
*A61K 6/08* (2006.01)
*A61K 6/00* (2006.01)
*A61K 6/02* (2006.01)
*A61K 6/083* (2006.01)

(52) U.S. Cl.
CPC ............... *A61K 6/08* (2013.01); *A61K 6/0088* (2013.01); *A61K 6/0091* (2013.01); *A61K 6/024* (2013.01); *A61K 6/083* (2013.01)

(58) Field of Classification Search
CPC ..... A61K 6/005; A61K 6/008; A61K 6/0052; A61K 6/083; A61K 2800/262; C08L 33/00
USPC ............................. 523/115, 216; 433/228.1
See application file for complete search history.

(56) References Cited

U.S. PATENT DOCUMENTS

| | | | |
|---|---|---|---|
| 4,567,030 A | 1/1986 | Yuasa et al. | |
| 6,232,367 B1 * | 5/2001 | Kobashigawa et al. | 523/116 |
| 7,678,843 B2 * | 3/2010 | Fusejima et al. | 523/117 |
| 2005/0020720 A1 * | 1/2005 | Dickens et al. | 523/115 |
| 2008/0319104 A1 | 12/2008 | Klapdohr et al. | |
| 2010/0304961 A1 * | 12/2010 | Kimura et al. | 502/160 |

FOREIGN PATENT DOCUMENTS

| | | | |
|---|---|---|---|
| JP | 60-011505 | * | 1/1985 |
| JP | 60-11505 | * | 1/1985 |
| JP | 2000-80013 | | 3/2000 |
| JP | 2002-138008 | | 5/2002 |
| JP | 2003-511400 | | 3/2003 |
| JP | 2007-532518 | | 11/2007 |

OTHER PUBLICATIONS

International Search Report dated Sep. 13, 2011 issued in corresponding international patent application No. PCT/JP2011/063337.
Color Science Association of Japan and Japanese Standards Association, JIS Z 8730, Color specification-Color difference of objects colors, Mar. 20, 2009. (Declaration of Translator with English translation of the relevant portion of this document on pp. 1228-1229).
Yong-Keun Lee, et al., "Measurement of Opalescence of Resin Composites," Dental Materials, 2005, vol. 21, pp. 1068-1074.
Supplementary European Search and Opinion dated Dec. 12, 2014 in corresponding European Patent Application No. 11795649.0 (7 pages).

* cited by examiner

*Primary Examiner* — Tae H Yoon
(74) *Attorney, Agent, or Firm* — Ostrolenk Faber LLP

(57) ABSTRACT

There is provided a dental composite restorative material that has an excellent opalescent effect, no paste stickiness, small polymerization shrinkage during curing and is suitable for the restoration of the incisal edge of a tooth. This dental composite restorative material comprises: (A) a polymerizable monomer, (B) a spherical silica-based particle [I] having an average particle diameter in the range of from 0.1 to 0.5 μm and a standard deviation of particle diameter distribution within 1.30, preferably a silica-titanium group oxide-composite oxide particle, (C) an organic-inorganic composite filler prepared by dispersing the above-described silica-based particle [I] in an organic resin matrix, and (D) a polymerization initiator.

4 Claims, No Drawings

DENTAL COMPOSITE RESTORATIVE MATERIAL

CROSS REFERENCE TO RELATED APPLICATIONS

The present application is a 35 U.S.C. §371 national phase conversion of PCT/JP2011/063337, filed Jun. 10, 2011, which claims priority to Japanese Patent Application No. 2010-189440, filed Aug. 26, 2010, and Japanese Patent Application No. 2010-139519, filed Jun. 18, 2010.

BACKGROUND OF THE INVENTION

1. Field of the Invention

This invention relates to a dental composite restorative material and, more particularly, to a dental composite restorative material that has good transparency and opalescent effect and that is able to give cosmetics when it is used for the restoration of the incisal edge of tooth.

2. Description of the Related Art

Since a dental composite restorative material is able to give color tone equivalent to natural tooth color or is easy to use for treatment, it has rapidly spread in recent years and is now applied mainly for treatment of front teeth. Further, a dental composite restorative material having excellent mechanical strength applicable for the restoration of posterior teeth subject to high occlusion pressure is being developed.

In the case of the restoration of teeth by a dental composite restorative material, not only the recovery of occlusion, but also cosmetics, that is, whether a tooth restored by a dental composite restorative material looks as a natural tooth is important. It is, therefore, required for a dental composite restorative material to reproduce precisely the color tone of the treated point of a tooth.

A natural tooth comprises dentine and enamel, and the color tone of natural teeth is originated mainly from dentine and is observed through transparent enamel. Enamel increases from the tooth neck toward the incisal edge. Particularly, a large part of the incisal edge is composed of enamel and has high transparency compared with the rest of the tooth and is known for the generation of characteristic milky-white light. That is to say, the incisal edge generates a characteristic light scattering phenomenon (opalescent effect) identical to the mineral opal, and light of short wavelength is reflected by scattering; on the other hand, light of long wavelength transmits. As a result, under a bright environmental light, bluish milky-white color is usually observed, which changes to an orange-tinged color tone depending on the viewing angle. For cosmetic restoration, delicate tone of such an incisal edge should be reproduced. Not only high transparency, but also an opalescent effect is required for a dental composite restorative material applied to such an incisal edge.

In general, a dental composite restorative material comprises a polymerizable monomer, a filler and a polymerization catalyst. The above described opalescent effect can be obtained depending on the selection of filler used. That is to say, it has been reported that an opalescent effect can be obtained by the addition of a spherical inorganic filler having a particle diameter of 0.2~0.6 µm (See Patent Publication (Toku-hyo) 2003-511400, claim) or addition of spherical inorganic filler having an average particle diameter of 0.18~0.28 µm (See Patent Publication (Toky-hyo) 2007-532518 at para. [0032]). Hereinafter, an inorganic filler having such an opalescent effect is referred to as "opalescence-giving filler." It is said that the opalescent effect can be clearly developed when the shape of the opalescence-giving filler is spherical as described above and its particle diameter distribution is sharper. Further, an inorganic filler having a small difference in the refractive index between the inorganic filler and the cured body of the polymerizable monomer is preferable, because it is possible to make the cured body of the restorative composite material highly transparent and to develop the opalescent effect easily. In this sense, a silica-based particle is suitable.

Patent Publication (Toky-hyo) 2007-532518 at para. [0040] describes that an organic-inorganic composite filler may be added as an optional additive other than the above-described opalescence-giving filler. However, this publication describes for an inorganic filler dispersed in the organic resin matrix in the organic-inorganic composite filler, only that pulverized glass, a silica particle, a radiopaque filler, etc. are used for the purpose of increasing mechanical strength or giving radiopacity, but never describes the dispersion of the opalescence-giving filler.

CITATION LIST

Patent Literature

PLT1: Patent Publication (Toku-hyo) 2003-511400
PLT2: Patent Publication (Toku-hyo) 2007-532518

BRIEF SUMMARY OF THE INVENTION

The present inventors have studied a dental composite restorative material using a silica-based particle as an opalescence-giving filler. As a result, we have found that when the average particle diameter of a silica-based particle is 0.1~0.5 µm, the cured body is not only highly transparent, but also develops the opalescent effect excellently. There are, however, problems in that, since the particle diameter of the silica particle is small, a paste containing such a silica particle is sticky and that by sole-use of such a silica particle, the filler-packing ratio cannot be increased, mechanical strength is deficient, polymerization shrinkage at the time of curing is large, etc.

It has been generally known that such problems as paste stickiness and polymerization shrinkage at the time of curing can be improved by the addition of an organic-inorganic composite filler to a dental composite restorative material. Therefore, we have studied a dental composite restorative material containing the above-described opalescence-giving filler by the use of various kinds of organic-inorganic composite fillers. As a result, we have found that the paste stickiness and polymerization shrinkage at the time of curing can be solved as expected by the addition of the organic-inorganic composite filler. On the other hand, when an organic-inorganic composite filler contains a generally-used dispersed inorganic filler that has been usually used for the improvement of mechanical strength or radiopacity, the opalescent effect is most drastically decreased. Accordingly, such a dental composite restorative material cannot give satisfactory cosmetics as the restoration of an incisal edge, and therefore, further improvement is required.

Based on the above-described background, a primary object of this invention is to provide a dental composite restorative material suitable for the restoration of an incisal edge, which has an excellent opalescent effect, little paste stickiness, and low polymerization shrinkage.

In view of the above-described problems, the present inventors have found that the above-described problems can be solved by the addition of an opalescence-giving filler as an inorganic filler of the organic-inorganic composite filler and have accomplished this invention.

The present invention relates to a dental composite restorative material comprising:
(A) a polymerizable monomer,
(B) a silica-based particle having average particle diameter of 0.1~0.5 μm and standard deviation of particle diameter distribution within 1.30,
(C) an organic-inorganic composite filler obtained by dispersing said silica-based particle in an organic resin matrix, and
(D) a polymerization initiator.

The dental composite restorative material of this invention has the advantageous effects that by addition of the organic-inorganic composite filler, a paste thereof has no stickiness, the polymerization shrinkage during curing is small, and its cured body has high transparency and an excellent opalescent effect. Accordingly, when the dental composite restorative material of this invention is used for the restoration of the incisal edge of a tooth, excellent cosmetics can be obtained and the usefulness is significant.

DETAILED DESCRIPTION OF INVENTION

The dental composite restorative material of this invention comprises a polymerizable monomer (A), a silica-based particle (B) having an opalescent effect and specific average particle diameter, an organic-inorganic composite filler (C), and a polymerization initiator (D). As used herein, the term "organic-inorganic composite filler" means a composite filler of a polymer with an inorganic filler. The dental composite restorative material of this invention has the advantageous effects that as the organic-inorganic composite filler is added, a paste thereof has no stickiness and the polymerization shrinkage during curing is small.

The principal characteristic of this invention is that an organic-inorganic composite filler of the same silica-based particle as that used in the above-described component (B) is used as an inorganic filler to be dispersed in the organic-inorganic composite filler (C). Thereby, the opalescent effect of the dental composite restorative material can be maintained to a high degree.

In the case of the addition of the organic-inorganic composite filler in a curable composition to which an opalescence-giving filler is added, when the refractive index of the inorganic filler added in the organic-inorganic composite filler is drastically different from that of the polymerizable monomer, the cured body of the curable composition loses transparency and cannot develop the opalescent effect. When the particle diameter of the inorganic filler is sufficiently smaller than the wavelength of visible light (0.005~0.09 μm), it cannot generate the effective light scattering, and cannot develop the opalescent effect, the transparency of a curable composition is good. However, also, in such a case, since the organic-inorganic composite filler having no opalescent effect occupies a significant volume in the cured body, the opalescence cannot be uniformly developed and the opalescent effect is thus weakened.

To the contrary, as described above, when an organic-inorganic composite filler in which the silica-based particle of the opalescence-giving filler is dispersed is used as an organic-inorganic composite filler, the cured body of the curable composition obtained can develop an opalescent effect also in the parts in which the organic-inorganic composite filler exists. The whole cured body therefore can develop the opalescent effect uniformly, and the problem of a decrease in the opalescent effect due to the inorganic filler in the aforementioned organic-inorganic composite filler can be solved.

Each of the components of the dental composite restorative material of this invention is described below:

(A) A Polymerizable Monomer:
In the dental composite restorative material of this invention, publicly-known polymerizable monomers can be used as a polymerizable monomer without particular limitation and, for example, a radical polymerizable monomer, cationic polymerizable monomer, etc. can be used. From the view point of dental use, a radical polymerizable monomer is preferable from the standpoint of polymerization rate, and polyfunctional ones are more preferable. A particularly preferable radical polymerizable monomer is a polyfunctional(meth)acrylate-series polymerizable monomer.

Polyfunctional(meth)acrylate-series polymerizable monomers are exemplified by the following (X)~(Z):
(X) Bifunctional Polymerizable Monomers;
(i) Aromatic Compound-Families;
2,2-bis(methacryloyloxyphenyl)propane,
2,2-bis[4-(3-(methacryloyloxy)-2-hydroxypropoxyphenyl)]propane,
2,2-bis(4-methacryloyloxyphenyl)propane,
2,2-bis(4-methacryloyloxypolyethoxyphenyl)propane,
2,2-bis(4-methacryloyloxydiethoxyphenyl)propane,
2,2-bis(4-methacryloyloxytetrarthoxyphenyl)propane,
2,2-bis(4-methacryloyloxypentaethoxyphenyl)propane,
2,2-bis(4-methacryloyloxydipropoxyphenyl)propane,
2(4-methacryloyloxydiethoxyphenyl)-2-(4-methacryloyloxytriethoxyphenyl)propane,
2(4-methacryloyloxydipropoxyphenyl)-2-(4-methacryloyloxytriethoxyphenyl)propane,
2,2-bis(4-methacryloyloxypropoxyphenyl)propane,
2,2-bis(4-methacryloyloxyisopropoxyphenyl)propane, and acrylates corresponding to these methacrylates;
diadducts obtained by addition reaction of methacrylates having an —OH group such as 2-hydroxyethylmethacrylate, 2-hydroxypropylmethacrylate, 3-chloro-2-hydroxypropylmethacrylate, or acrylates having an —OH group corresponding to these methacrylates, with a di-isocyanate compound having an aromatic group, such as di-isocyanate methyl benzene, 4,4'-diphenyl methane di-isocyanate, etc.

(ii) Aliphatic Compound-Families;
Ethylene glycol dimethacrylate,
Diethylene glycol dimethacrylate,
Triethylene glycol dimethacrylate,
Tetraethylene glycol dimethacrylate,
Neopentyl glycol dimethacrylate,
1,3-butanediol dimethacrylate,
1,4-butanediol dimethacrylate,
1,6-hexanediol dimethacrylate,
1,2-bis(3-methacryloyloxy-2-hydroxypropoxy)ethyl, and acrylates corresponding to these methacrylates; and
diadducts obtained by the addition reaction of methacrylates having an —OH group such as 2-hydroxyethylmethacrylate, 2-hydroxypropylmethacrylate, 3-chloro-2-hydroxypropylmethacrylate, or acrylates having an —OH group corresponding to these methacrylates, with a di-isocyanate compound such as hexamethylene diisocyanate, trimethyhexamethylene diisocyanate, diisocyanatemethylcyclohexane, isophorone diisocyanate, methylene bis(4-cyclohexylisocyanate), etc.

(Y) Trifunctional Polymerizable Monomers:
trimethylolpropane trimethacrylate,
trimethylolethane trimethacrylate,
pentaerythritol trimethacrylate, trimethylolmethane trimethacrylate and acrylates corresponding to these methacrylates, etc.

(Z) Tetrafunctional Polymerizable Monomers:
pentaerythritol tetramethacrylate, pentaerythritol tetraacrylate; and
diadducts obtained by addition reaction of a diisocyanate compound such as diisocyanate methyl benzene, diisocyanatemethylcyclohexane, isophoronediisocyanate, hexamethylenediisocyanate, trimethylhexamethylenediisocyanate, methylene bis(4-cyclohexylisocyanate), 4,4-diphenylmethanediisocyanate or tolylene-2,4-diisocyanate with a glycidol dimethacrylate or glycidol diacrylate, etc.

The refractive index (25° C.) of a cured body of these polyfunctional(meth)acrylate-family polymerizable monomers is in the range of usually 1.45~1.60, preferably 1.52~1.56. It is preferable that an appropriate polyfunctional (meth)acrylate-family polymerizable monomer is selected from those corresponding to the refractive index (25° C.) of the silica-based particle used (the refractive index of silica is 1.45 and the refractive index of the composite oxide of a silica-titanium group oxide is usually 1.48~1.58), so that the difference in the refractive index between the polyfunctional (meth)acrylate-family polymerizable monomer and silica-based particle becomes small. (Specific value of difference in the refractive index is described infra.) It may be acceptable to adjust the desired refractive index to the desired one as a whole by combination of two or more polymerizable monomers. In general, many aromatic polymerizable monomers show a high refractive index, and many aliphatic polymerizable monomers show a low refractive index. It is preferable to adjust the refractive index by adding usually 20% by weight and above of an aromatic polymerizable monomer to the total amount of polymerizable monomer.

And, if necessary, monofunctional(meth)acrylate monomer, such as methacrylate, ethyl methacrylate, isopropyl methacrylate, hydroxyethyl methacrylate, tetrahydrofurfuryl methacrylate, glycidyl methacrylate, etc. and acrylates corresponding to these methacrylates, or a radical polymerizable monomer other than the above-described (meth)acrylate monomer may be used as a polymerizable monomer.

The silica-based particle (B) having an average particle diameter of 0.1~0.5 μm and standard deviation of particle diameter distribution within 1.30;
A silica-based particle having an average particle diameter of 0.1~0.5 μm is added to the dental composite restorative material of this invention for the purpose of giving an opalescent effect. It is important in this invention that the average particle diameter of the silica-based particle is 0.1~0.5 μm for the development of the opalescent effect. That is to say, the development of the opalescent effect is caused by the occurrence of diffraction-interference according to Bragg's Law and enhancement of the light of a specific wavelength. By the addition of the silica-based particle having the above-described particle diameter to the dental composite restorative material of this invention, such a phenomenon can be developed in the cured body of the dental composite restorative material. In order to improve significantly the opalescent effect, the average particle diameter of the silica-based particle is more preferably 0.12~0.3 μm, and specifically more preferably 0.14~0.28 μm.

Relating to the average particle diameter of the silica-based particle, the particle diameter means a primary particle diameter. It is important that the primary particle diameter of the silica-based particle is in the range of the above-described average values. If it is a particle which is satisfied with such a condition, it may be acceptable that individualities of primary particles exist more or less as an agglomerated particle. It is, however, preferable that the silica-based particles exist as independent particles as much as possible and specifically preferable that an agglomerated particle having a particle diameter of 10 μm and above is less than 10% by volume.

According to this invention, the average particle diameter of a particle means the average value obtained by a method in which a photograph of a powder is taken by a scanning electron microscope, and more than 30 particles observed in a unit visual field of the photograph are selected, and average values of each particle diameter (maximum diameter) are obtained.

The shape of the silica-based particle is inevitably spherical, because light scattering is uniform and brilliant coloring is developed. When the particle size of the silica-based particle is uniform, the uniformity of scattered light rises and a good opalescent effect can be obtained. It is, therefore, preferable to use a silica-based particle, the standard deviation of particle size distribution of which is in the range of 1.30, and more preferably 1.20.

In this invention, the shape of the silica-based particle may be an approximate sphere, but is not necessarily a perfect sphere. A silica-based particle the average uniformity of which is 0.6 and above, more preferably 0.8 and above, may be used in this invention. In general, the average uniformity can be obtained by a method in which a photograph of the particle is taken by a scanning electron microscope, and for each of the particles present in a unit visual field of the photograph (more than 30 particles) the particle diameter crossing at right angles to its maximum diameter is divided by its maximum diameter.

On the other hand, the standard deviation of particle size distribution means the value obtained by a method in which a photograph of a powder is taken by a scanning electron microscope, and more than 30 particles observed in a unit visual field of the photograph are selected, and obtained according to the calculation formula described below: [0032]

$$\text{Standard deviation} = \frac{\bar{x} + \sigma_{n-1}}{\bar{x}}$$

Herein, $$\bar{x} = \frac{\sum_{i=1}^{n} x_i}{n} \text{ (number average)},$$

$$\sigma_{n-1} = \sqrt{\frac{\sum_{i=1}^{n}(x_i - \bar{x})^2}{n-1}}$$

(n: number of particle. $x_i$: particle diameter of the ith particle (maximum diameter))

In this invention, the "silica-based particle" is exemplified by crystal silica such as quartz, amorphous silica, a composite metal oxide containing silica as a main component with another metal oxide, etc. As amorphous silica, those produced by a wet process or dry process may be used. A composite metal oxide containing silica as a main component with another metal oxide is preferable, because the refractive index of the filler can be controlled by changing the compounding ratio of the silica to the other metal oxide. Among them, a composite oxide of silica with an oxide of a titanium group element (elements belonging to the IVa-group of the periodic table) (hereinafter referred to as "silica-titanium group oxide-composite oxide particle") is particularly preferable, because it gives radiopacity to the dental composite restorative material.

A silica-titanium group oxide-composite oxide particle is exemplified by silica-titania, silica-zirconia, silica-titania-zirconia, etc. A silica-zirconia is most preferable because of its high radiopacity. The compounding ratio of silica to the oxide of the titanium group element is not particularly limited in the silica-titanium group oxide-composite oxide particle; but the silica-titanium group oxide-composite oxide particle having a silica content of 70~95 mol % and a titanium group oxide content of 5~30 mol % is preferable from the view point that they can give sufficient radiopacity and set the refractive index in the desired range. In the case of silica-zirconia, its refractive index (25° C.) can be adjusted usually in the range of 1.48~1.58 by changing the compounding ratio of silica content to zirconia content.

A small amount of a metal oxide other than the silica and titanium group oxides may be mixed with these silica-titanium group oxide-composite oxides; specifically, alkali metal oxides such as sodium oxide, lithium oxide, etc. may be added within 10 mol %.

The method of production of these silica-titanium group oxide-composite oxide particles is not particularly limited, but, for example, a sol-gel method comprising adding a mixed solution containing a hydrolyzable organosilicon compound and a hydrolyzable organotitanium-group metal compound in an alkaline solvent to prepare a mixture, hydrolyzing the mixture and depositing a reaction product may be preferably adopted.

Such a silica-based particle may be subjected to surface treatment with a silane coupling agent. By surface treatment with a silane coupling agent, the interfacial strength between a cured part of polymerizable monomer (A) and the silica-based particle is significantly improved. Typical silane coupling agents are exemplified by an organosilicon compound such as γ-methacryloyloxyalkyltrimethoxysilane, hexamethyldisilazane, etc. The amount of these silane coupling agents used for surface treatment is not particularly limited, but its optimum amount may be determined appropriately after experimental confirmation of physical properties such as the mechanical strength of the dental composite restorative material obtained. A preferable range of the amount of silane coupling agent may be in the range of 0.1~15 parts by weight to 100 parts by weight of the particle.

As described above, when the transparency of a cured body is high, the opalescent effect can be developed brilliantly. It is, therefore, preferable that a silica-based particle is selected so as not to damage transparency, that is, so that the difference in the refractive index (25° C.) between a cured body of) polymerizable monomer (A) and the silica-based particle is 0.1 and below, more preferably 0.05 and below.

According to this invention, the amount of addition of silica-based particle (B) is preferably 100~400 parts by weight per 100 parts by weight of the polymerizable monomer (A). By the addition of the silica-based particle (B) in the amount of 100 parts by weight and above, the opalescent effect is significantly developed. On the other hand, it is generally difficult if particles having an average particle diameter of 0.1~0.5 μm are added in large amounts beyond 400 parts by weight. When the silica-based particle having a large difference in refractive index (25° C.) between a cured body of the polymerizable monomer (A) and the silica-based particle is used, there are possibilities that the transparency of the cured body may be lowered and the opalescent effect not sufficiently developed. Taking the above-described facts into consideration, the amount of addition of a silica-based particle (B) is preferably 150~350 parts by weight per 100 parts by weight of the polymerizable monomer (A) and more preferably 180~320 parts by weight per 100 parts by weight of the polymerizable monomer (A).

An organic-inorganic composite filler (C) obtained by dispersing the silica-based particle in an organic resin matrix: As afore-mentioned, in this invention, an organic-inorganic composite filler (C) obtained by making use of the silica-based particle, which is the afore-mentioned opalescence-giving filler as inorganic fillers dispersed in an organic resin matrix, is used. The detailed information on the silica-based particle is completely the same as the afore-mentioned explanation on component (B). The silica-based particle dispersed in the organic-inorganic composite filler is preferably the same type of silica-based particle used as the component (B), but different types of silica-based particle may be used so long as they are within the range prescribed.

For an organic resin matrix of an organic-inorganic composite filler (C), a homopolymer of the same polymerizable monomer as those described as the afore-mentioned polymerizable monomer (A) or copolymer of plural kinds of polymerizable monomers may be used without limitation.

The content of the silica-based particle in the organic-inorganic composite filler is not particularly limited, but is preferably similar to that of the opalescence-giving filler (B) dispersed in the polymerizable monomer (A). This is because, since opalescence-giving fillers are dispersed uniformly in a dental composite restorative material of this invention, an opalescent effect can be brilliantly developed. Specifically, the content of the silica-based particle is preferably 50~85% by weight to the total weight of organic-inorganic composite filler. When the content of the silica-based particle is less than 50% by weight, there are possibilities that the development of the above-described opalescent effect may be lowered, and the mechanical strength of a cured body of a dental composite restorative material of this invention may not be sufficient. On the other hand, it is generally difficult to disperse silica-based particles uniformly in large amounts beyond 85% by weight in an organic-inorganic composite filler. Further a preferable content of the silica-based particles is 50~80% by weight to organic-inorganic composite filler, and most preferably 60~78% by weight to organic-inorganic composite filler.

As the above-described organic-inorganic composite filler (C), it is necessary to use such an organic-inorganic composite filler (C) that the difference in refractive index (25° C.) between the organic-inorganic composite filler (C) and the cured body of the polymerizable monomer (A) is adjusted to be 0.1 and below, more preferably 0.05 and below so as not to lower the transparency of the dental composite restorative material due to the addition thereof, thereby making it possible to develop the opalescent effect significantly. Adjustment of the refractive index of such an organic-inorganic composite filler (C) may be carried out by adjusting appropriately the types, compound ratio, etc., of the silica-based particles and organic resin matrix used.

In this invention, the organic-inorganic composite filler (C) may be produced according to a general method of producing an organic-inorganic composite filler comprising the steps of mixing an inorganic filler, a polymerizable monomer, and a polymerization initiator in given amounts thereof to prepare a polymerizable composition, polymerizing the polymerizable composition by heating or irradiation with light, etc., to prepare a polymerized composition and then pulverizing the polymer composition. As a polymerization initiator, publicly-known polymerization initiators such as photopolymerization initiator and thermal polymerization initiator may be used without limitation, but a thermal polymerization initiator may be preferably used.

In the method for the production of the above-described organic-inorganic composite filler, pulverization of the polymer obtained by polymerization of the polymerizable composition is carried out by means of a pulverizing mill such as a ball mill, vibration ball mill, jet mill, etc. Because of impact or friction during pulverization, fillers are heated to high temperatures inevitably and locally and change their original color to yellow. Such yellowing is remarkably decreased by decolorization (Toku-Kai-Hei No. 10-114616, Publication). Alternatively, such yellowing can be significantly decreased by the production of the above-described organic-inorganic composite filler by a gentle method without severe pulverization using the above-described pulverizing mill. The method comprises the steps of: aggregating previously an inorganic filler to obtain inorganic aggregated particles, impregnating a polymerizable monomer into the inorganic aggregated particles to prepare an inorganic aggregated particles-impregnated polymerizable monomer, and polymerizing said inorganic aggregated particles-impregnated polymerizable monomer (Toku-Kai 2008-37952). However, such yellowing is hard to be completely suppressed or there may be a case where the above described methods for suppression of yellowing cannot be adopted because of a complexity of operations, etc.

When the incisal edge of a tooth is restored with a dental composite restorative material obtained by making use of such a yellowish organic-inorganic composite filler as above mentioned, the cosmetics are significantly damaged. This is because that since the incisal edge of a tooth is remarkably superior in transparency as afore-mentioned, a yellow-tinged incisal edge of a tooth is distinctive, even if it is slight. However, according to this invention, since the silica-based particles which are opalescence-giving fillers are dispersed in an organic-inorganic composite filler, a blue-color giving opalescent effect developed by the silica-based particles becomes an opposite color to the above-described yellow in particles to weaken such yellowish color. As a result, the development of an opalescent effect by silica-based particles (B) is maintained to be excellent in the dental composite restorative material, and the cosmetics of the dental composite restorative material are highly maintained.

Specifically, in the case of an organic-inorganic filler produced by the afore-mentioned general method, that is, a method comprising the steps of polymerizing a polymerizable composition containing an inorganic filler, a polymerizable monomer and a polymerization initiator to form a polymer, then pulverizing the polymer by means of a pulverizing mill, the chromaticity index (b*) showing blue-yellow in the background color of black is on the order of −0.5~2.0. However, when the organic-inorganic composite filler is produced by making use of the afore-mentioned opalescence-giving filler as the inorganic filler according to this invention, even by the general method, it is possible to lower the b* of the organic-inorganic composite filler to −2.5 and below, particularly −3.0~−4.5. It is, therefore, possible to use the organic-inorganic composite filler produced by the afore-mentioned general method. Of course, when the organic-inorganic composite filler produced by a method which is hard to generate yellowing in the afore-mentioned organic resin matrix is used as an organic-inorganic composite filler, it is preferable, because the development of the opalescent effect of the dental composite restorative material is excellent.

In this invention, the average particle diameter of the organic-inorganic composite filler (C) is not particularly limited, but may be preferably 2~100 μm, more preferably 5~500 μm, and most preferably 15~30 μm from the view point that the mechanical strength of the cured body is increased or the workability of the curable paste is good.

A publicly-known additive can be added to the organic-inorganic composite filler (C) in a range that does not damage its effect. Specifically, a pigment, a polymerization inhibitor, a fluorescence agent, etc., are exemplified. An organic-inorganic composite filler may be subjected to cleaning or a surface treatment by silane coupling agent, etc., before it is used as a dental composite restorative material.

In the dental composite restorative material of this invention, the amount of addition of the organic-inorganic composite filler (C) may be preferably 50~450 parts by weight per 100 parts by weight of the polymerizable monomer (A) from the view point that paste stickiness is resolved and polymerization shrinkage during polymerization is decreased. Further, the amount of addition of the organic-inorganic composite filler (C) may be preferably 70~400 parts by weight per 100 parts by weight of the polymerizable monomer (A). Furthermore, the amount of addition of the organic-inorganic composite filler (C) may be most preferably 90~340 parts by weight per 100 parts by weight of the polymerizable monomer (A).

In the dental composite restorative material of this invention, the amount of total contents of the silica-based particle] (B) and the organic-inorganic composite filler (C) (may be in the range of the contents of each of them, but it is preferable that each of the silica-based particle (B) and the silica-based particle in the organic-inorganic composite filler (C) is dispersed uniformly in the dental composite restorative material in order to obtain a good opalescent effect. From the view point that the silica-based particle (B) and the organic-inorganic composite filler (C) are dispersed excellently, it is preferable that the total amount of the silica-based particle (B) and the organic-inorganic composite filler (C) is suppressed to 730 parts by weight and below per 100 parts by weight of the polymerizable monomer (A), more preferably to 700 parts by weight and below, and most preferably to 660 parts by weight and below. In order to improve the opalescent effect sufficiently, the total amount of the silica-based particle (B) and the organic-inorganic composite filler (C) may be preferably 270 parts by weight and above per 100 parts by weight of the polymerizable monomer (A).

Since the dental composite restorative material of this invention is used for a dental cavity direct filling material, a photopolymerization initiator (composition) or chemical polymerization initiator (composition) may be preferable and a photopolymerization initiator (composition) is preferable being that no mixing-operation is required and it is easy to use.

As the polymerization initiator used for photopolymerization, there can be exemplified: benzoinalkyl ethers such as benzoinmethyl ether, benzomethyl ether, benzoinisopropyl ether; benzyl ketals such as benzyldimethyl ketal and benzyldiethyl ketal; benzophenones such as benzophenone, 4,4'-dimethylbenzophenone and 4-methacryloxybenzophenone; α-diketones such as diacetyl, 2,3-pentadionbenzyl, camphorquinone, 9,10-phenanthraquinone and 9,10-anthraquinone;
thioxanthone compounds such as 2,4-diethoxythioxanthone, 2-chlorothioxanthone and methylthioxanthone; and bisacylphosphine oxides such as
bis(2,6-dichlorobenzoyl)phenylphosphine oxide,
bis(2,6-dichlorobenzoyl)-2,5-dimethylphenylphosphine oxide, bis(2,6-dichlorobenzoyl)-4-propylphenylphosphine oxide, bis(2,6-dichlorobenzoyl)-1-naphthylphosphine oxide, and bis(2,4,6-trimethylbenzoyl)-phenylphosphine oxide.

A reducing agent is often added to the photopolymerization initiator. Such a reducing agent is exemplified by tertiary amines such as 2-(dimethylamino) ethyl methacrylate, 4-dimethylaminoethyl benzoate and N-methyldiethanolamine, etc; aldehydes such as lauryl aldehyde, dimethylaminobenzaldehyde and terephthalaldehyde; and sulfur-containing compounds such as 2-mercaptobenzooxazole, 1-decanethiol, thiosalicylic acid and thiobenzoic acid, etc.

A photoacid generator is often added to the above-described photopolymerization initiator and reducing compound. Such a photoacid generator may be exemplified by diaryliodonium salt-family compounds, sulfonium salt-family compounds, sulfonate compounds, and halomethyl-substituted-S-triazine derivatives, pyridium salt-family compounds, etc.

The polymerization initiator may be used singly or mixed together in two or more different kinds. With respect to the amount of addition of polymerization initiator, the effective amount thereof may be selected according to objects, but may be preferably usually 0.01~10 parts by weight, and more preferably 0.1~5 parts by weight per 100 parts by weight of the polymerizable monomer.

Another Additive

To the dental composite restorative material of this invention a publicly-known additive in addition to the above-described components (A)~(D) may be added within a range that does not damage its effect. Such an additive is specifically exemplified by a polymerization inhibitor, a pigment, a UV-absorber, etc. It is also effective for the purpose of viscosity control, etc., that fillers having an average particle diameter sufficiently smaller than the wavelength of light (specifically an average particle diameter: 0.005~0.09 μm), which are unlikely to affect color tone or transparency, are added.

Opalescence of a Cured Body of a Dental Composite Restorative Material:

A cured body of the dental composite restorative material of this invention has excellent transparency and good opalescence. That is to say, a specimen 1 mm thick of the cured body of the dental composite restorative material of this invention has a contrast ratio showing high transparency of usually 0.3 and below and more preferably 0.25 and below. Herein the contrast ratio is a value obtained by a method in which the Y-values for tristimulus values are measured by the use of a spectrophotometer in the background colors of black and white and obtained according to the following formula:

Contrast ratio=Y-value in the background color of black/Y-value in the background color of white.

A specimen 1 mm thick has an excellent value of $\Delta C^*$ (an index showing opalescent effect) of usually 18 and above, preferably 20 and above, and more preferably 25.5 and above. Herein the $\Delta C^*$ can be obtained by the following formula. An orange color of transmitted light is indicated by $a^*$ showing red-green and a blue color of reflected light is indicated by $b^*$ showing blue-yellow:

$$\Delta C^* = \sqrt{(a^*_b - a^*_w)^2 + (b^*_b - b^*_w)^2}$$

($a^*_b$, $b^*_b$: chromaticity index in the background color of black, $a^*_w$, $b^*_w$: chromaticity index in the background color of white)

Herein, $\Delta C^*$ is a value obtained by deleting item of an Brightness index from a calculation formula of color difference by L*a*b*-color system described in [Color specification-Color difference of objects colors] (JIS Z 8730 (2009)) and is a quantity corresponding to the distance between two points in a plane of a*-b* and shows the opalescent effect the color tone of which is different depending on the back color. $\Delta C^*$ is measured by a reflection mode at a C-light source of a spectrophotometer (that is, light reflected from a specimen is measured, when light is applied at an angle of 45 degrees to a normal line of a specimen), and is calculated according to the above-described formula. An orange color of light transmitted through a specimen, which is one of the characteristics of opalescent effect, is indicated by $a^*$ showing red-green and a blue color of light reflected from a specimen is indicated by $b^*$ showing blue-yellow.

It has been well known in the dental field that the value obtained from such a relation between $a^*$ and $b^*$ as described above is an index showing the excellence of opalescent effect as described in, for example, Toku-Hyo No. 2003-511400, and Y. K. Lee et al., "Measurement of opalescence of resin composite," Dent Mater, 2005, vol. 21, pp. 1068-1078, etc. In this literature, a value corresponding to a value of chromaticity index ($a^*$, $b^*$) in the background color of white in the calculation formula of the above-described $\Delta C^*$ is measured in the mode of transmission (that is to say, when light is applied from the direction of a normal line of a specimen, light transmitted through a specimen is measured). However, even if it is measured in the mode of reflection in the background color of white, all optical wavelengths of light transmitted through the specimen are reflected to be measured. Accordingly, the value of $\Delta C^*$ obtained is satisfactorily correlated with the index of opalescent effect described in the above-described literature.

For the spectrum reflectance of a specimen 1 mm thick in the background color of black, the maximum value can be obtained at a wavelength of 420~470 nm. The condition "in the background color of black" means a measurement of light reflected from a specimen. Since the body of a dental composite restorative material of this invention has excellent transparency and opalescent effect, it shows a maximum at a wavelength of 420~470 nm showing a blue color.

The dental composite restorative material of this invention is usually prepared by weighing given amounts of each of the afore-mentioned indispensable components and each of the optional components to prepare a mixture thereof, mixing sufficiently to form a paste and, if necessary, deaerating the paste under reduced pressure to remove air.

The dental composite restorative material of this invention is used in accordance with a general method of the use of a filling composite resin. Specifically, a method is exemplified, in which in a case where the polymerization initiator (D) is a photopolymerization initiator, after a cavity of a tooth to be restored is treated with an appropriate pretreatment agent or adhesives, the dental composite restorative material is directly filled into the cavity thus pretreated, forming the dental composite restorative material filled into the cavity in the shape of a tooth, irradiating the dental composite restorative material filled into the cavity with powerful light by means of a specialized dental irradiator, and polymerizing to cure the dental composite restorative material filled into the cavity. The part of the tooth to which the dental composite restorative material is applied is not specifically limited, but may be preferably the part to which an opalescent effect is required; and it is optimum to use it for the incisal edge of a tooth.

EXAMPLES

Hereinafter, this invention will be further described by use of Examples and Comparative Examples. However, this invention shall not be limited by these Examples.

Methods of measurement of various kinds of physical properties in this invention are as described below:

(1) The Standard Deviation of an Average Primary Particle Diameter and Particle Diameter Distribution of a Silica-Based Particle:

A photograph of powder was taken by a scanning-type electron microscope (manufactured by JEOL Ltd. under the trade name of T-330A), and a number of particles (50) observed in a unit visual field and particle diameters were measured. Average particle diameter and standard deviation were then calculated on the basis of the measured values in accordance with the following formula:

$$\text{Standard deviation} = \frac{\bar{x} + \sigma_{n-1}}{\bar{x}} \quad \text{Equation 2}$$

Herein, $$\bar{x} = \frac{\sum_{i=1}^{n} x_i}{n} \text{ (number average)},$$

$$\sigma_{n-1} = \sqrt{\frac{\sum_{i=1}^{n}(x_i - \bar{x})^2}{n-1}}$$

(n: number of particle, $x_i$: particle diameter of the ith particle diameter))

(2) Average Uniformity of a Silica-Based Particle:

A photograph of a powder was taken by a scanning-type electron microscope (manufactured by JEOL Ltd. under the trade name of T-330A), and a number of particles (n: 50) observed in a unit visual field was measured, the maximum diameter, that is, major axis (Li) of a particle, and the diameter crossing at right angles to the major axis, that is, the minor axis (Bi), were obtained, and an average uniformity was calculated in accordance with the following formula:

$$\text{Average uniformity} = \frac{\sum_{i=1}^{n} Bi/Li}{n} \quad \text{Equation 3}$$

(3) Measurement of the Specific Surface Area of a Silica-Based Particle:

Measurement was carried out in accordance with BET equation by making use of a specific surface area-measuring apparatus (sold under the trademark FLOW SORB II 2300, as manufactured by SHIMADZU CORPORATION). A mixed gas of 30% of nitrogen and 70% of helium was used, and liquid nitrogen was used as a cooling medium.

(4) Measurement of the Refractive Index of a Silica-Based Particle:

In a thermostat maintained at 23° C., 1 g of silica-based particles was dispersed in 50 ml of toluene anhydride in a sample bottle of 100 ml to obtain a dispersion. 1-bromotoluene was added dropwise gradually into the dispersion, while agitating the dispersion with a stirrer. When the transparency of the dispersion reaches a maximum, the refractive index of the dispersion was measured by an Abbe's refractometer, and the value obtained was taken as the refractive index of the silica-based particle.

(5) Evaluation of Yellowness of an Organic-Inorganic Composite Filler:

Organic-inorganic composite fillers were sprayed onto an adhesive face of a 10×10 mm (length×breadth) black tape (carbon tape) and excess fillers were blown away by air. This procedure was repeated three times. Then, the face on which the fillers are adhered was put on a polyester film, and a measurement was carried out in the background color of black by the use of a color-difference meter (manufactured by Tokyo Denshoku Co., Ltd. under the trade name TC-1800MK I I). In order to evaluate the yellowness of the organic-inorganic composite filler, b* showing blue-yellow was compared in the background color of black.

(6) Evaluation of the Opalescent Effect of the Dental Composite Restorative Material:

A paste of the dental composite restorative material was put into a mold having a 7 mm×1 mm hole, and both faces of the hole were covered by pressuring with a polyester film.

Thereafter, both faces were irradiated with light for 30 seconds for each of both faces by means of a dental irradiator (manufactured by TOKUYAMA under the trade name Power-Light) to cure the paste. The cured paste was then removed from the mold as a specimen. For each specimen, measurements were carried out on the bases of a visual field of two (2) degrees in the mode of reflection at a light source of C in the background colors of black (L*:0.9, a*:−1.4, b*:−0.2) and white (a ceramic standard white board manufactured by Tokyo Denshoku co., Ltd. L*:97.2, a*:−0.2, b*:0.3). Then, ΔC* was obtained in accordance with the following formula and was taken as an index of the opalescent effect. Herein, an orange color of transmitted light which is a characteristic of the opalescent effect is indicated by a* showing red-green, and a blue color of reflected light is indicated by b* showing blue-yellow.

$$\Delta C^* = \sqrt{(a^*_b - a^*_w)^2 + (b^*_b - b^*_w)^2}$$

($a^*_b$, $b^*_b$: chromaticity index in the background color of black, $a^*_w$, $b^*_w$: chromaticity index in the background color of white)

Visual evaluations were carried out on the basis of the following indexes:

⊚: color development of strong blue was observed in the background color of black.

○: color development of weak but blue was observed in the background color of black.

Δ: color development of blue was scarcely observed in the background color of black.

X: no color development of blue was observed in the background color of black.

(7) Evaluations of the Transparency of a Dental Composite Restorative Material:

Similar to (6), a cured body of the dental composite restorative material was prepared. Then, for the cured body, Y-values for tristimulus values are measured by the use of a color difference meter in the background colors of black and white. Contrast ratio was calculated in accordance with the following formula and was taken as an index of transparency:

Contrast ratio=Y-value in the background color of black/Y-value in the background color of white.

Handling of a paste of a dental composite restorative material Evaluations were carried out in accordance with the following indexes:
◉: a good handling without stickiness
○: a slight stickiness or roughness observed, but no problems in practical handling.
X: stickiness or roughness observed.
Polymerizable monomers, polymerization initiators and various kinds of additives used in Examples and Comparative Examples are as described below:
Polymerizable Monomers:
   2,2-bis[(3-methacryloyloxy-2-hydroxypropyloxy)phenyl]propane (hereinafter abbreviated as bis-GMA)
   Triethyleneglycol dimethacrylate (hereinafter abbreviated as 3G).
   2,2-bis(4-methacryloyloxypolyethoxyphenyl)propane (hereinafter abbreviated as D-2,6E)
   1,6-bis(methacryloxyethyloxycarbonylamino)trimethylhexane (hereinafter abbreviated as UDMA)
Polymerization Initiators:
   Azobisisobutyronitrile (hereinafter abbreviated as AIBN)
   Camphorquinone (hereinafter abbreviated as CQ)
   N,N-dimethylamino p-ethylbenzoate (hereinafter abbreviated as DMBE)
Polymerization Inhibitors:
   Hydroquinone monomethylether (hereinafter abbreviated as HQME])
   Dibutylhydroxytoluene (hereinafter abbreviated as BHT)
UV-Absorber:
   2-hydroxy-4-methoxybenzophenone (hereinafter abbreviated as BS110)

Production Example 1

Production of Organic Resin Matrices

Each of the polymerizable monomers as shown in Table-1 was mixed to prepare matrices M-1~M-4 used in the Examples and Comparative Examples.

TABLE 1

| name of matrix | polymerizable monomer | refractive index of cured body |
|---|---|---|
| M-1 | bis-GMA(30)/3G (70) | 1.528 |
| M-2 | UDMA(70)/3G(30) | 1.510 |
| M-3 | bis-GMA(60)/3G (40) | 1.546 |
| M-4 | D-2,6E(75)/3G (25) | 1.553 |

Production Example 2

Production of Silica-Based Particles

Silica-based particles used in the Examples and Comparative Examples were prepared by the method described below:
2-1) Production of Spherical Silica-Titania Particles Having an Average Primary Particle Diameter of 0.25 μm
170 g of tetraethylsilicate (manufactured by COLCOAT CO., LTD. under the product name Ethylsilicate 28) were mixed with 400 g of methanol to prepare a mixture, to which 5 g of 0.04% aqueous solution of hydrochloric acid were added, and hydrolyzed at a temperature of 30° C. while agitating for about one hour to prepare a solution (solution-1). Thereafter, a solution obtained by dissolving 27 g of tetrabutyl titanate and 10 g of sodium methylate methanol solution (concentration: 30% by weight) in 200 g of isopropyl alcohol was mixed with the solution-1 while agitating to prepare a mixed solution of tetraethylsilicate with tetrabutyl titanate. Next, 1000 g of methanol were introduced into a glass container equipped with an agitating device (internal volume: 3 L), then 250 g of 25% by weight of ammonia aqueous solution were added to prepare an ammoniacal alcohol solution. 2 g of tetraethylsilicate for the preparation of seeds of silica particles were added to the ammoniacal alcohol solution and agitated for 30 minutes, thereafter, the above-described mixed solution of tetraethylsilicate with tetrabutyl titanate was added dropwise for about five hours.

The temperature of the reactor was maintained at 40° C. throughout the reaction. After the completion of the reaction, solvent was distilled off from a milky-white reaction liquid and dried, and then sintering was carried out at a temperature of 950° C. for one hour to obtain silica-titania particles (PF-1). The particle diameter distribution of the silica-titania particles (PF-1) is 0.23~0.27 μm, and the average primary particle diameter is 0.25 μm. The shape of the silica-titania particles (PF-1) is spherical by SEM observation. The silica-titania particles (PF-1) thus obtained were subjected to surface-treatment with γ-methacryloyloxypropyltrimethoxysilane. Various kinds of physical properties of the particles obtained are shown in Table 2.

2-2) Production of Spherical Silica-Zirconia Particles Having an Average Primary Particle Diameter of 0.19 μm
120 g of tetraethylsilicate (manufactured by COLCOAT CO., LTD. under the product name [Ethylsilicate 28) were mixed with 400 g of isobutyl alcohol (manufactured by Tonen Chemical Corporation, old name: Tonen Petrochemicals Corporation) to prepare a mixture, to which 5 g of a 0.05% dilute aqueous solution of sulfuric acid were added, and hydrolyzed at a temperature of 40° C. while agitated for about one hour to prepare a solution (solution 2). Thereafter, a solution obtained by dissolving 25 g of tetrabutyl zirconate (manufactured by Nippon Soda Co., Ltd.) and 10 g of sodium methylate methanol solution (concentration: 28% by weight) in 200 g of isopropyl alcohol was mixed with the solution 2 while agitating to prepare a mixed solution of tetraethylsilicate with tetrabutyl zirconate. Next, 1000 g of methanol and 250 g of 25% by weight of ammonia aqueous solution were introduced into a glass container equipped with an agitating device (internal volume: 3 L) to prepare an ammoniacal alcohol solution. Then, 4 g of tetraethylsilicate were added to the ammoniacal alcohol solution obtained while agitating, after agitation for 30 minutes, the above-described mixed solution of tetraethylsilicate with tetrabutyl zirconate was added dropwise for about six hours.

The temperature of the reactor was maintained at 40° C. throughout the reaction. After completion of the reaction, solvent was distilled off from a milky-white reaction liquid and dried, and then sintering was carried out at a temperature of 950° C. for one hour to obtain silica-zirconia particles (PF-2). The particle diameter distribution of the silica-zirconia particles (PF-2) is 0.16~0.20 μm, and the average primary particle diameter is 0.19 μm. The shape of the silica-zirconia particles (PF-2) is spherical. The silica-zirconia particles (PF-2) thus obtained were subjected to surface-treatment with γ-methacryloyloxypropyltrimethoxysilane. Various kinds of physical properties of the particles obtained are shown in Table 2.

2-3) Production of Spherical Silica-Titania Particles Having an Average Primary Particle Diameter of 0.08 µm 170 g of tetraethylsilicate (manufactured by COLCOAT CO., LTD. under the product name [Ethylsilicate 28] were mixed with 400 g of methanol to prepare a mixture, to which 5 g of 0.04% aqueous solution of hydrochloric acid were added, and hydrolyzed at a temperature of 30° C. while agitating for about one hour to prepare a solution (solution 3). Thereafter, a solution obtained by dissolving 26 g of tetrabutyl titanate (manufactured by Nippon Soda Co., Ltd.) and 10 g of sodium methylate methanol solution (concentration: 28% by weight) in 200 g of isopropyl alcohol was mixed with the solution 3 while agitating to prepare a mixed solution of tetraethylsilicate with tetrabutyl titanate. Next, 1000 g of methanol and 250 g of 25% by weight of ammonia aqueous solution were introduced into a glass container equipped with an agitating device (internal volume: 3 L) to prepare an ammoniacal alcohol solution. Then, 2 g of tetraethylsilicate for the preparation of seeds of silica particles were added to the ammoniacal alcohol solution while agitating. After agitation for 30 minutes, the above-described mixed solution of tetraethylsilicate with tetrabutyl titanate was added dropwise for about five hours.

The temperature of the reactor was maintained at 40° C. throughout the reaction. After completion of the reaction, solvent was distilled off from a milky-white reaction liquid and dried, and then sintering was carried out at a temperature of 1000° C. for one hour to obtain silica-titania particles (PF-3). The particle diameter distribution of the silica-titania particles (PF-3) is 0.072~0.095 µm, and the average primary particle diameter is 0.079 µm. The shape of the silica-zirconia particles (PF-3) is spherical by SEM observation. The silica-titania particles (PF-3) thus obtained were subjected to surface treatment with γ-methacryloyloxypropyltrimethoxysilane. Various kinds of physical properties of the particles obtained are shown in Table 2.

2-4) Production of Spherical Silica-Zirconia Particles Having an Average Primary Particle Diameter of 0.06 µm 80 g of tetraethylsilicate (manufactured by COLCOAT CO., LTD. under the product name [Ethylsilicate 28] were mixed with 400 g of isobutyl alcohol (manufactured by Tonen Chemical Corporation) to prepare a mixture, to which 5 g of a 0.05% dilute aqueous solution of sulfuric acid were added, and hydrolyzed at a temperature of 40° C. while agitating for about one hour to prepare a solution (solution-4). Thereafter, a solution obtained by dissolving 21 g of tetrabutyl zirconate (manufactured by Nippon Soda Co., Ltd.) and 13 g of sodium methylate methanol solution (concentration: 28% by weight) in 200 g of isobutyl alcohol was mixed with the solution 4 while agitating to prepare a mixed solution of tetraethylsilicate with tetrabutyl zirconate. Next, 1000 g of methanol and 200 g of 25% by weight of ammonia aqueous solution were introduced into a glass container equipped with an agitating device (internal volume: 3 L) to prepare an ammoniacal alcohol solution. Then, the above-described mixed solution of tetraethylsilicate with tetrabutyl zirconate was added dropwise to the ammoniacal alcohol solution obtained for about three hours, while agitating.

The temperature of the reactor was maintained at 40° C. throughout the reaction. After completion of the reaction, solvent was distilled off from a milky-white reaction liquid, dried, and then sintering was carried out at a temperature of 950° C. for one hour to obtain silica-zirconia particles (PF-4). The particle diameter distribution of the silica-zirconia particles (PF-4) is 0.04~0.08 µm, and the average primary particle diameter thereof is 0.064 µm. The shape of the silica-zirconia particles (PF-4) is spherical. The silica-zirconia particles (PF-4) thus obtained were subjected to surface treatment with γ-methacryloyloxypropyltrimethoxysilane. Various kinds of physical properties of the particles obtained are shown in Table 2.

2-5) Production of Spherical Silica-Zirconia Particles Having an Average Primary Particle Diameter of 0.4 µm 120 g of tetraethylsilicate (manufactured by COLCOAT CO., LTD. under the product name [Ethylsilicate 28] were mixed with 400 g of isobutyl alcohol (manufactured by Tonen Chemical Corporation) to prepare a mixture, to which 5 g of a 0.05% dilute aqueous solution of sulfuric acid were added, and hydrolyzed at a temperature of 40° C. while agitating for about one hour to prepare a solution (solution 5). Thereafter, a solution obtained by dissolving 24 g of tetrabutyl zirconate (manufactured by Nippon Soda Co., Ltd.) and 10 g of sodium methylate methanol solution (concentration: 28% by weight) in 200 g of isobutyl alcohol was mixed with the solution 5 while agitating to prepare a mixed solution of tetraethylsilicate with tetrabutyl zirconate. Next, 1000 g of methanol and 250 g of 25% by weight of ammonia aqueous solution were introduced into a glass container equipped with an agitating device (internal volume: 3 L) to prepare an ammoniacal alcohol solution. Then, 4 g of tetraethylsilicate were added to the ammoniacal alcohol solution, while agitating. After agitating for 30 minutes, the above-described mixed solution of tetraethylsilicate with tetrabutyl zirconate was added dropwise to the ammoniacal alcohol solution for about six hours.

The temperature of the reactor was maintained at 40° C. throughout the reaction. After the completion of the reaction, solvent was distilled off from a milky-white reaction liquid, dried, and then sintering was carried out at a temperature of 950° C. for one hour to obtain silica-zirconia particles (PF-5). The particle diameter distribution of the silica-zirconia particles (PF-5) is 0.36~0.43 µm, and the average primary particle diameter thereof is 0.40 µm. The shape of the silica-zirconia particles (PF-5) is spherical. The silica-zirconia particles (PF-5) thus obtained were subjected to surface-treatment with γ-methacryloyloxypropyltrimethoxysilane. Various kinds of physical properties of the particles obtained are shown in Table 2.

2-6) Production of Spherical Silica-Titania Particles Having an Average Primary Particle Diameter of 0.6 µm 120 g of tetraethylsilicate (manufactured by COLCOAT CO., LTD. under the product name [Ethylsilicate 28]) were mixed with 400 g of methanol to prepare a mixture, to which 5 g of a 0.04% aqueous solution of hydrochloric acid were added, and hydrolyzed at a temperature of 30° C. while agitating for about one hour to prepare a solution (solution 6). Thereafter, a solution obtained by dissolving 20 g of tetrabutyl titanate and 10 g of sodium methylate methanol solution (concentration: 30% by weight) in 100 g of isopropyl alcohol were mixed with the solution 6 while agitating to prepare a mixed solution of tetraethylsilicate with tetrabutyl titanate. Next, 1000 g of methanol and 250 g of 25% by weight of ammonia aqueous solution were introduced into a glass container equipped with an agitating device (internal volume: 3 L) to prepare an ammoniacal alcohol solution. Then, 2 g of tetraethylsilicate for the preparation of seeds of silica particles were added to the ammoniacal alcohol solution while agitating, after agitation for 30 minutes, the above-described mixed solution of tetraethylsilicate with tetrabutyl titanate was added dropwise for about five hours.

The temperature of the reactor was maintained at 40° C. throughout the reaction. After the completion of the reaction, solvent was distilled off from a milky-white reaction liquid, dried, and then sintering was carried out at a temperature of 950° C. for one hour to obtain silica-titania particles (PF-6).

The particle diameter distribution of the silica-titania particles (PF-6) is 0.56~0.64 μm, and the average primary particle diameter is 0.61 μm. The shape of the silica-zirconia particles (PF-6) is spherical by SEM observation. The silica-titania particles (PF-6) thus obtained were subjected to surface-treatment with γ-methacryloyloxypropyltrimethoxysilane. Various kinds of physical properties of the particles obtained are shown in Table 2

TABLE 2

| name of silica-based particle | composition of silica-based particle | average primary particle diameter (μm) | standard deviation | average uniformity | specific surface area (m²/g) | refractive index (25° C.) |
|---|---|---|---|---|---|---|
| PF-1 | SiO₂/TiO₂/Na₂O | 0.25 | 1.02 | 0.98 | 13.1 | 1.525 |
| PF-2 | SiO₂/ZrO₂/Na₂O | 0.19 | 1.05 | 0.95 | 15.2 | 1.522 |
| PF-3 | SiO₂/TiO₂/Na₂O | 0.079 | 1.06 | 0.93 | 42.3 | 1.523 |
| PF-4 | SiO₂/ZrO₂/Na₂O | 0.064 | 1.05 | 0.95 | 46.7 | 1.510 |
| PF-5 | SiO₂/ZrO₂/Na₂O | 0.40 | 1.11 | 0.97 | 6.3 | 1.519 |
| PF-6 | SiO₂/TiO₂/Na₂O | 0.61 | 1.16 | 0.98 | 3.4 | 1.526 |

Production Example 3

Production of Organic-Inorganic Fillers

Each of the silica-base particles shown in Table 3 was weighed and put in a mortar, and was added gradually in a matrix in which AIBN had been previously dissolved as a polymerization initiator in a weight ratio of 0.5% shown in Table-3, and mixed together to prepare a paste. Each of the pastes was polymerized at a temperature of 95° C. in a nitrogen atmosphere for one hour to obtain a cured polymerized composition. The cured polymerized composition thus obtained was pulverized by using a roll crusher and then further pulverized for 30 minutes under such conditions that the cured polymerized composition was put in a 400 mL pot together with ten (10) zirconia balls having a diameter of 25 mm in a vibration ball mill (manufactured by CHUO KAKOKI CO., LTD., under the trade name New-Right Mill) to obtain organic-inorganic composite fillers. The organic-inorganic composite fillers thus obtained were subjected to surface-treatment with γ-methacryloyloxypropyltrimethoxysilane.

50 g of each of the organic-inorganic composite fillers were added into a mixed liquid of 75 mL of ethanol and 6.6 mL of 30% hydrogen peroxide water, refluxed at a temperature of 80° C., then filtered, cleaned, and dried to obtain decolorized organic-inorganic composite fillers. Each of the decolorized organic-inorganic composite fillers thus obtained was subjected to surface treatment with γ-methacryloyloxypropyltrimethoxysilane. Various kinds of physical properties of the particles obtained are shown in Table 3.

TABLE 3

| name of organic-inorganic composite filler | matrix | silica-based particle | packing ratio (wt %) | average particle diameter | refractive index (25° C.) | evaluation of yellowness (b* in the back of black) |
|---|---|---|---|---|---|---|
| CF-1 | M-1 | PF-1 | 75% | 29 μm | 1.526 | −3.8 |
| CF-2 | M-1 | PF-1 | 62% | 28 μm | 1.526 | −3.0 |
| CF-3 | M-2 | PF-1 | 75% | 25 μm | 1.521 | −3.1 |
| CF-4 | M-1 | PF-2 | 70% | 27 μm | 1.524 | −3.5 |
| CF-5 | M-1 | PF-2 | 75% | 22 μm | 1.524 | −3.9 |
| CF-6 | M-1 | PF-2 | 78% | 25 μm | 1.523 | −4.2 |
| CF-7 | M-3 | PF-2 | 75% | 28 μm | 1.528 | −4.1 |
| CF-8 | M-1 | PF-5 | 75% | 27 μm | 1.521 | −2.7 |
| CF-9 | M-4 | PF-5 | 75% | 18 μm | 1.528 | −2.6 |
| CF-10 | M-3 | PF-3 | 67% | 24 μm | 1.531 | −1.9 |
| CF-11 | M-2 | PF-4 | 66% | 21 μm | 1.510 | −1.8 |
| CF-12 | M-1 | PF-6 | 77% | 29 μm | 1.526 | −1.8 |
| CF-13 | M-1 | — | — | 29 μm | 1.528 | −1.5 |

In the case of the organic-inorganic composite fillers CF-1~9 shown in Table 3, the inorganic filler added in an organic-inorganic composite filler to be added as the (C) component in the dental composite restorative material of this invention satisfies the requirements silica-based particles. On the other hand, in the case of the organic-inorganic composite fillers CF-10~12 shown in Table 3, the inorganic filler does not satisfy the above-described requirements for silica-based particles. Compared with the organic-inorganic composite fillers CF-10~12, the organic-inorganic composite fillers CF-1~9 have a smaller b* and are less yellowish.

The CF-13 shown in Table 3 contains no silica-based particle and is an organic filler produced in accordance with methods similar to those for the production of other organic-inorganic composite fillers and has a big b* and is strongly yellowish.

Examples 1~6

To matrix M-1, 0.2% by weight of CQ, 0.3% by weight of DMBE, 0.15% by weight of HQME, 0.02% by weight of BHT and 0.5% by weight of BS110 were added to prepare a homogenous polymerizable monomer composition. Next, each of the silica-based particles (B) and the organic-inorganic composite fillers (C) shown in Table 4 were weighed and put in a mortar. The above-described matrix M-1 was added gradually in the mortar under red light, and then mixed sufficiently in a dark place to prepare a homogenous curable paste. Thereafter, the paste was deaerated under reduced pressure to remove bubbles and to prepare a dental composite restorative material. For the dental composite restorative materials thus obtained, each of the physical properties thereof was evaluated on the basis of the afore-mentioned methods. Compositions and Results obtained are shown in Table 4.

Examples 7~11

Pastes were prepared in such a manner as above-described for Examples 1~6, except that each of the dental composite restorative materials was prepared by the use of (A) matrix M-3, (B) silica-based particle PF-2, and (C) organic-inorganic composite fillers CF-7, CF-4, or CF-6 in such an amount of addition as shown in Table 4. For the dental composite restorative materials thus obtained, each of the physical properties thereof was evaluated. Results obtained are shown in Table 4.

Examples 12~14

Pastes were prepared in such a manner as above-described for Examples 1~6, except that each of the dental composite restorative materials was prepared by using (A) matrix M-4, (B) silica-based particle PF-5, and (C) organic-inorganic composite filler CF-9 in such an amount of addition as shown in Table 4. For the dental composite restorative materials thus obtained, each of the physical properties thereof was evaluated. Results obtained are shown in Table 4.

Examples 15~16

Pastes were prepared in such a manner as above-described for Examples 1~6, except that (C) organic-inorganic composite filler CF-5 or CF-8 was used instead of (C) organic-inorganic composite filler CF-1. For the dental composite restorative materials thus obtained, each of the physical properties thereof was evaluated. Results obtained are shown in Table 4.

TABLE 4

|  | (A) matrix | (B) silica-based particle | (C) organic-inorganic composite filler | packing ratio of filler⋇ | handling of paste | difference in refractive index⋇⋇ | ratio of contrast | chromaticity index in the back of black $a^*_b$ | $b^*_b$ | chromaticity index in the back of white $a^*_w$ | $b^*_w$ | opalescent effect $\Delta C^*$ | visual evaluation |
|---|---|---|---|---|---|---|---|---|---|---|---|---|---|
| Example 1 | M-1 (100) | PF-1 (280) | CF-1 (140) | 81% | ◎ | 0.002 | 0.138 | 4.52 | −19.62 | −0.88 | 6.37 | 26.5 | ◎ |
| Example 2 | M-1 (100) | PF-1 (300) | CF-1 (95) | 80% | ◎ | 0.002 | 0.110 | 4.91 | −19.78 | −1.01 | 6.59 | 27.0 | ◎ |
| Example 3 | M-1 (100) | PF-1 (340) | CF-1 (100) | 82% | ○ | 0.002 | 0.141 | 3.88 | −18.06 | −0.81 | 5.71 | 24.2 | ○ |
| Example 4 | M-1 (100) | PF-1 (190) | CF-1 (350) | 84% | ◎ | 0.002 | 0.265 | 1.98 | −14.09 | −0.78 | 5.87 | 20.1 | ○ |
| Example 5 | M-1 (100) | PF-1 (280) | CF-2 (140) | 81% | ◎ | 0.002 | 0.132 | 4.38 | −19.53 | −0.80 | 6.07 | 26.1 | ◎ |
| Example 6 | M-1 (100) | PF-1 (280) | CF-3 (140) | 81% | ◎ | 0.007 | 0.136 | 4.45 | −19.61 | −0.84 | 6.21 | 26.4 | ◎ |
| Example 7 | M-3 (100) | PF-2 (280) | CF-7 (140) | 81% | ◎ | 0.018 | 0.111 | 5.09 | −20.98 | −1.05 | 6.83 | 28.5 | ◎ |
| Example 8 | M-3 (100) | PF-2 (240) | CF-7 (150) | 80% | ◎ | 0.018 | 0.115 | 4.99 | −20.48 | −1.01 | 6.78 | 27.9 | ◎ |
| Example 9 | M-3 (100) | PF-2 (160) | CF-7 (200) | 78% | ○ | 0.018 | 0.147 | 3.72 | −17.26 | −0.79 | 5.75 | 23.4 | ○ |
| Example 10 | M-3 (100) | PF-2 (280) | CF-4 (140) | 81% | ◎ | 0.022 | 0.118 | 5.18 | −20.95 | −1.03 | 6.73 | 27.8 | ◎ |
| Example 11 | M-3 (100) | PF-2 (280) | CF-6 (140) | 81% | ◎ | 0.023 | 0.113 | 5.19 | −21.01 | −1.09 | 6.81 | 28.5 | ◎ |
| Example 12 | M-4 (100) | PF-5 (280) | CF-9 (140) | 80% | ◎ | 0.025 | 0.135 | 3.97 | −18.81 | −0.84 | 5.78 | 25.1 | ○ |
| Example 13 | M-4 (100) | PF-5 (190) | CF-9 (210) | 80% | ◎ | 0.025 | 0.176 | 3.78 | −17.56 | −0.79 | 5.80 | 23.8 | ○ |
| Example 14 | M-4 (100) | PF-5 (240) | CF-9 (80) | 76% | ○ | 0.025 | 0.119 | 4.37 | −18.79 | −0.83 | 5.83 | 25.2 | ○ |

TABLE 4-continued

| | (A) matrix | (B) silica-based particle | (C) organic-inorganic composite filler | packing ratio of filler* | handling of paste | difference in refractive index** | ratio of contrast | chromaticity index in the back of black a*$_b$ | b*$_b$ | chromaticity index in the back of white a*$_w$ | b*$_w$ | opalescent effect ΔC* | visual evaluation |
|---|---|---|---|---|---|---|---|---|---|---|---|---|---|
| Example 15 | M-1 (100) | PF-1 (280) | CF-5 (140) | 81% | ◎ | 0.004 | 0.145 | 4.45 | −19.02 | −0.86 | 6.02 | 25.6 | ◎ |
| Example 16 | M-1 (100) | PF-1 (280) | CF-8 (140) | 81% | ◎ | 0.007 | 0.182 | 3.42 | −15.81 | −0.76 | 5.86 | 22.1 | ○ |

*packing ratio of filler: weight % of (B) silica-based particle and (C) organic-inorganic composite filer, contained in paste
**difference in refractive index: difference between refractive index of cured body of matrix (A) and refractive index of organic-inorganic composite filler (C)

In all of Examples 1~16, dental composite restorative materials having good handling of the pastes thereof, small contrast ratio, strong opalescent effect, and maximum spectral reflectance in the background color of black in the vicinity of 440 nm, were obtained. Specifically, Examples 1, 2, 5, 6, 7, 8, 10, 11, and 15 exhibited strong opalescent effect and were specifically suitable. This is because that each of a silica-based particle of component (B) and a silica-based particle contained in component (C) organic-inorganic composite filler has an appropriate particle diameter and an amount of addition of each of (B) a silica-based particle and (C) an organic-inorganic composite filler is remarkably proper, respectively.

Comparative Examples 1~9

Pastes were prepared in such a manner as above-described for Examples 1~6, except that each of composite restorative materials was composed of each of the components shown in Table 5 and prepared dental composite restorative materials. For the dental composite restorative materials thus obtained, each of the physical properties thereof was evaluated. Results obtained are shown in Table 5.

TABLE 5

| | (A) matrix | (B) silica-based particle | (C) organic-inorganic composite filler | packing ratio of filler* | handling of paste | difference in refractive index** | ratio of contrast | chromaticity index in the back of black a*$_b$ | b*$_b$ | chromaticity index in the back of white a*$_w$ | b*$_w$ | opalescent effect ΔC* | visual evaluation |
|---|---|---|---|---|---|---|---|---|---|---|---|---|---|
| Comparative Example 1 | M-3 (100) | PF-3 (280) | CF-1 (140) | 81% | ◎ | 0.020 | 0.104 | 0.49 | −11.89 | −0.38 | 2.99 | 14.9 | X |
| Comparative Example 2 | M-2 (100) | PF-4 (280) | CF-1 (140) | 81% | ◎ | 0.016 | 0.113 | 0.41 | −11.61 | −0.27 | 2.83 | 14.5 | X |
| Comparative Example 3 | M-1 (100) | PF-6 (280) | CF-1 (140) | 81% | ◎ | 0.002 | 0.381 | −0.51 | −6.41 | −0.95 | 3.80 | 10.2 | X |
| Comparative Example 4 | M-1 (100) | PF-1 (280) | CF-13 (140) | 81% | ◎ | 0 | 0.127 | 0.91 | −10.29 | −0.81 | 5.98 | 16.4 | X |
| Comparative Example 5 | M-1 (100) | PF-2 (280) | CF-13 (140) | 81% | ◎ | 0 | 0.109 | 1.01 | −11.04 | −0.79 | 5.94 | 17.1 | X |
| Comparative Example 6 | M-1 (100) | PF-5 (280) | CF-13 (140) | 81% | ◎ | 0 | 0.125 | 0.84 | −9.83 | −0.81 | 5.85 | 15.8 | X |
| Comparative Example 7 | M-1 (100) | PF-1 (280) | CF-10 (140) | 81% | ◎ | 0.003 | 0.152 | 1.10 | −12.29 | −0.51 | 5.18 | 17.5 | Δ |
| Comparative Example 8 | M-2 (100) | PF-1 (280) | CF-11 (140) | 81% | ◎ | 0 | 0.139 | 1.18 | −12.50 | −0.51 | 5.20 | 17.8 | Δ |
| Comparative Example 9 | M-1 (100) | PF-1 (280) | CF-12 (140) | 81% | ◎ | 0.002 | 0.399 | −0.58 | −5.97 | −0.96 | 3.16 | 9.1 | X |

*packing ratio of filler: weight % of (B) silica-based particle and (C) organic-inorganic composite filer, contained in paste
**difference in refractive index: difference between refractive index of cured body of matrix (A) and refractive index of organic-inorganic composite filler (C)

Comparative Examples 1~3 are examples using as silica-based particle (B), a silica-based particle that is not an opalescence-giving filler. Comparative Examples 4~6 are examples in which an organic filler containing no inorganic filler but produced in a method of production similar to that of the above-described organic-inorganic composite filler is used, instead of the organic-inorganic composite filler (C). Comparative Examples 7~9 are examples in which an inorganic filler which is not an opalescence-giving filler is used as organic-inorganic composite filler (C). Each of the composite restorative materials obtained does not exhibit such excellent opalescence as that of the afore-mentioned Examples.

The invention claimed is:

1. A dental composite restorative material comprising;
(A) a polymerizable monomer, the refractive index (25° C.) of a cured body of which is 1.52~1.56,
(B) a spherical silica-based particle [I] having an average particle diameter in the range of from 0.1 to 0.5 µm and a standard deviation of particle diameter distribution within 1.30,
(C) an organic-inorganic composite filler prepared by dispersing the above-described silica-based particle [I] in an organic resin matrix, and
(D) a photopolymerization initiator, wherein said photopolymerization initiator is the only polymerization initiator;
wherein said (A), (B), (C) and (D) are homogeneously mixed with each other, said mixture constituting 100 parts by weight of the polymerizable monomer (A); from 100 to 400 parts by weight of the spherical silica-based particle [I] having an average particle diameter in the range of from 0.1 to 0.5 µm and a standard deviation of particle diameter distribution within 1.30 (B); from 50 to 450 parts by weight of said organic-inorganic composite filler prepared by dispersing the silica-based particle [I] in an organic resin matrix (C); and from 0.01 to 10 parts by weight of said photopolymerization initiator (D),
and wherein a difference in a refractive index between a cured body of said (A) polymerizable monomer and said (C) organic-inorganic composite filler is ≤0.1, a contrast ratio of a cured body of the composite restorative material is 0.3 and below, and $\Delta C^*$ as obtained by the following formula is 20 and above;

$$\Delta C^* = \sqrt{(a^*_b - a^*_w)^2 + (b^*_b - b^*_w)^2}$$

wherein $a^*_b$, $b^*_b$: represent a chromaticity index in the background color of black; $a^*_w$, $b^*_w$: represent a chromaticity index in the background color of white, and spectral reflectance in the background color of black is maximum at a wavelength of from 420 to 470 nm.

2. A dental composite restorative material as claimed in claim 1, wherein said silica-based particle [I] is a silica-titanium group oxide-composite oxide particle.

3. A dental composite restorative material as claimed in claim wherein said dental composite restorative material is used for restoration of incisal edge of a tooth.

4. A dental composite restorative material as claimed in claim 2, wherein said dental composite restorative material is used for restoration of incisal edge of a tooth.

* * * * *